United States Patent [19]
Neuenhofer et al.

[11] Patent Number: 5,858,668
[45] Date of Patent: Jan. 12, 1999

[54] HOMOGENEOUS GENE PROBE TEST USING A RECEPTOR DIRECTED AGAINST THE LABEL

[76] Inventors: Stephan Neuenhofer, Rotenberg 19, 35037, Marburg; Heinz-Juergen Skrzipczyk, Forsthausweg 11, 63263, Zeppelinheim; Norbert Madry, Höhenweg 68, 35041, Marburg; Reinhard Kasmarker, Höhenweg 2e, 35041, Marburg; Thomas Leutsch, Am Ziegenberg 8, 35041, Marburg; Eugen Uhlmann, Zum Talblick 31, 61479, Glashütten, all of Germany

[21] Appl. No.: 712,094

[22] Filed: Sep. 16, 1996

[30] Foreign Application Priority Data

Sep. 14, 1995 [DE] Germany ............ 195 34 122.8

[51] Int. Cl.⁶ ............ C12Q 1/68; G01N 33/53; C07H 21/04
[52] U.S. Cl. ............ 435/6; 435/7.1; 536/24.3; 935/7; 935/77; 935/78
[58] Field of Search ............ 435/4, 6, 7.1; 935/7, 935/77, 78; 536/22.1, 24.3–24.33

[56] References Cited

U.S. PATENT DOCUMENTS 4,743,535  5/1988  Carrico .................................. 435/6

FOREIGN PATENT DOCUMENTS 0 212 951  3/1987  European Pat. Off. .
0 313 219  9/1987  European Pat. Off. .
0 273 115  7/1988  European Pat. Off. .
0 281 390  9/1988  European Pat. Off. .
0 310 312  4/1989  European Pat. Off. .
0 407 816  1/1991  European Pat. Off. .
0 602 524  6/1994  European Pat. Off. .
89/02896  4/1989  WIPO .

OTHER PUBLICATIONS

Arrand et al in Nucleic Acid Hybridization: A Practical Approach, IRL Press, Washington D.C. (1985) pp. 42–45.
W.P. Collins, "Alternative Immunoassays", John Wiley and Sons, (1985). Table of Contents.
S. L. Beaucage et al., "Tetrahedron Report Number 329", Tetrahedron, vol. 49, No. 10, (1993), pp. 1925–1963.
L. J. Arnold Jr., "Assay Formats Involving Acridinium–Easter Labeled DNA Probes", Clin. Chem., vol. 35, No. 8, (1989), pp. 1588–1594.
J. Goodchild, "Conjugates of Oligonucleotides and Modified Oligonucleotides: A Review of Their Synthesis and Properties", Bioconjugate Chemistry, vol. 1, No. 3, (May/Jun. 1990), pp. 165–187.
J. A. Matthews et al., "Enhanced Chemiluminescent Method for the Detection of DNA Dot–Hybridization Assays", Analytical Biochemistry, vol. 151, (1985), pp. 205–209.

*Primary Examiner*—W. Gary Jones
*Assistant Examiner*—Debra Shoemaker
*Attorney, Agent, or Firm*—Foley & Lardner

[57] ABSTRACT

A homogeneous gene probe test, which is based on altering the signal of the nonhybridized gene probe by a receptor directed against the label on the gene probe is described.

4 Claims, 4 Drawing Sheets

1. Hybridization  FIG. 1(a) PRIOR ART
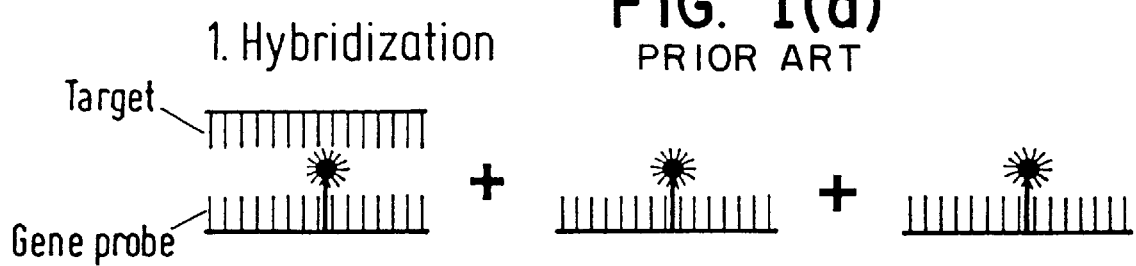
2. Selective hydrolysis  FIG. 1(b) PRIOR ART
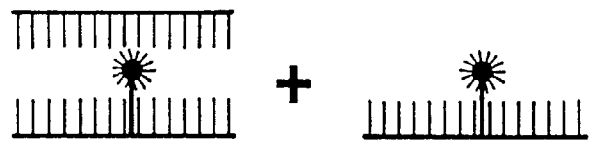
FIG. 1(c) PRIOR ART
3. Measurement
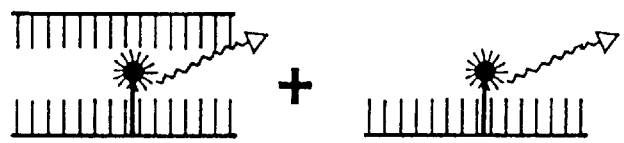

5'-GGC CGT TAC CCC ACC TAC TAG CTA AT [MOD]-3'

1. Hybridization

2. Quench

3. Measurement

1. Hybridization

2. Selective hydrolysis

3. Quench

Anti-label receptor

4. Measurement

HOMOGENEOUS GENE PROBE TEST USING A RECEPTOR DIRECTED AGAINST THE LABEL

BACKGROUND OF THE INVENTION

1. Field of the Invention

The invention relates to a homogeneous gene probe test, which is based on altering the signal of the non-hybridized gene probe by means of a receptor directed against the label.

2. Description of Background Art

Gene probe assays already have been described in the literature in various embodiments. More frequently used embodiments are the hybridization protection assay (Clin. Chem. 35/8, 1989, 1588–1594), the kissing probes technique (Nachr. Chem. Tech. Lab. 37/7, 1989, 698) and the energy transfer principle.

A very general principle of a gene probe assay according to the prior art is represented in FIGS. 1(a)–1(c): in the first step, target sequence and labeled gene probe are hybridized with one another, wherefrom double-stranded constructs result if there is sufficient homology of the two sequences. Moreover, as a rule, however, non-hybridized single-stranded portions of the gene probe also remain. In the second step, a selective hydrolysis is carried out, which comprises, on account of the conditions selected, essentially the label of the single-stranded gene probe being attacked, while the label of the double-stranded construct is largely protected from hydrolytic attack. Thus in the third step essentially the signal produced by the label bound in the double-stranded construct is then measured.

A disadvantage of the above method is that, despite the treatment with the selection reagent (step 2), a remnant of single-stranded gene probe having an intact label remains, which distorts the measurement.

The present invention is therefore based on the object of making available a method for the determination of a nucleic acid sequence (a "gene probe assay") in which the non-hybridized labeled gene probe contributes to a smaller extent to undesired signal formation than in the method according to the prior art. In particular, the improvement aimed at should make possible an improved homogeneous test procedure. The homogeneous test procedure is fundamentally characterized by the absence of a physical separation step between the nucleic acid hybridization and the signal detection. In such a method, according to the prior art, a particularly severe interfering effect has to be taken into account due to the non-hybridized labeled gene probe.

The object was surprisingly achieved by employing in the method according to the invention a receptor which can bind to the label and as a result of the binding detectably alters, for example attenuates ("quenches") the signal to be attributed to the label. By means of the method according to the invention described below, it is therefore possible significantly to reduce the interfering effect due to the non-hybridized labeled gene probe and thereby to improve the sensitivity and specificity of the test system decisively.

SUMMARY OF THE INVENTION

Thus, the present invention relates to an improvement in a method of detecting a target nucleotide sequence in a sample, the method comprising contacting a sample suspected of containing a target nucleotide sequence with a labeled gene probe capable of hybridizing with the target nucleotide sequence so that the target nucleotide sequence hybridizes with part, but not all of said labeled gene probe in the sample, wherein the improvement comprises:

(a) adding to the sample containing the target nucleotide sequence and hybridized labeled gene probe and non-hybridized gene probe, a receptor which binds the non-hybridized labeled gene probe, whereby the binding of the receptor to the label on the non-hybridized gene probe alters the signal generated by the label on the non-hybridized gene probe; and (b) detecting the labeled gene probe that is hybridized to said target nucleotide sequence.

In yet another embodiment, the invention relates to the above method further comprising incubating said non-hybridized gene probe with a selection reagent thereby partly inactivating said label on said non-hybridized gene probe. The receptor may be selected from the group consisting of a monoclonal antibody, a polyclonal antibody, an antibody fragment, a chemically modified antibody and a chemically modified antibody fragment. The label on the gene probe may be selected from the group consisting of labels capable of fluorescence, phosphorescence, chemiluminescence, bioluminescence or electroluminescence.

In one embodiment, the label is selected from the group consisting of an acridinium ester, an acridinium acylsulfonamide, a luminol, an isoluminol or a derivative thereof, a dioxetane, a luciferin, an oxalic acid ester and an oxamide.

In another embodiment, the label is an enzyme.

BRIEF DESCRIPTION OF THE DRAWINGS

FIGS. 1(a)–1(c) are schematic drawings of a prior art gene probe assay in which in the first step, a target sequence and labeled gene probe are hybridized with one another, wherefrom double stranded constructs result if there is sufficient homology of the two sequences. Non-hybridized single-stranded portions of the gene probe remain. In a second step, a selective hydrolysis is carried out, which comprises, on account of the conditions selected, essentially the label of the single-stranded gene probe being attacked, while the label of the double-stranded construct is largely protected from hydrophilic attack. In the third step, the signal produced by the label bound in the double-stranded construct is measured.

DETAILED DESCRIPTION OF THE INVENTION

Figure 2:
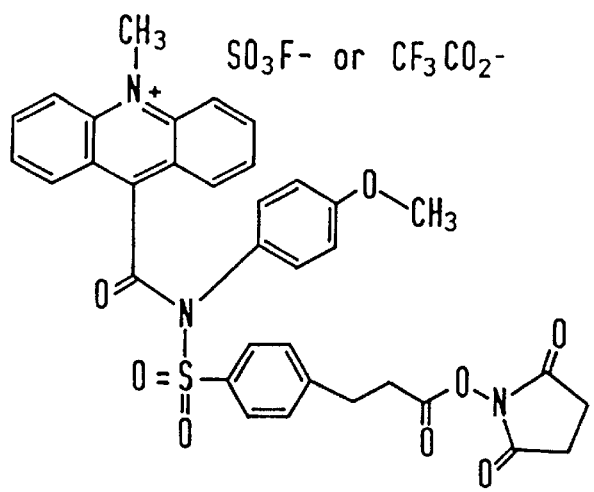
FIG. 2 shows the chemical structure of acridinium acylsulfonamide.

The present invention thus relates to a method for the determination of a nucleic acid sequence (=target sequence), in which a sample suspected of containing the target sequence is brought into contact with a gene probe suitable for the determination of this target sequence such that the target sequence and the gene probe hybridize with one another, which comprises, additionally (a) adding a receptor which binds to the label of an optionally excess fraction of the gene probe not hybridized to the target sequence, whereby the signal to be attributed to the label is qualitatively and/or quantitatively altered and (b) qualitatively or quantitatively detecting the signal to be attributed to the label using a method suitable for this purpose.

By "sample" is meant any plant, animal or viral material containing DNA or RNA. A label is "qualitatively or quantitatively altered" if its signal is diminished, quenched or completely extinguished. "Qualitative or quantitative" detection refers to visual or automated assessments based upon the magnitude (strength) or number of signals generated by the label.

The present invention furthermore relates to a method in which, in an additional step, the label of an optionally excess, nonhybridized gene probe is partly or totally inactivated by incubation with a selection reagent. "Total" inactivation means about 100% inactivation and partial inactivation is less than about 100% inactivation.

A preferred embodiment of the present invention comprises the incubation with the selection reagent taking place first and then the addition of the receptor.

A method is furthermore preferred in which the receptor is a monoclonal or polyclonal antibody, an antibody fragment, a chemically modified antibody or a chemically modified antibody fragment, if the antigen-binding capacity after the chemical modification is retained to an adequate extent.

Methods according to the invention which are furthermore preferred comprise the label selected from the group of labels capable of fluorescence, phosphorescence, chemiluminescence, bioluminescence or electroluminescence.

In a particularly preferred embodiment of the present invention, the label is an acridinium ester, an acridinium acylsulfonamide, a luminol, an isoluminol or a derivative thereof, a dioxetane, a luciferin, an oxalic acid ester or an oxamide.

A method is also preferred in which the label is an enzyme.

Labels

Suitable labels are all labels capable of fluorescence, phosphorescence, chemiluminescence, bioluminescence or electroluminescence, which on account of their chemical structure can interact with a nucleic acid double strand, for example by intercalating in the double-strand, in such a way that the binding of a receptor directed against this group is made difficult in comparison with the binding to the corresponding single strand-bound group. Particularly suitable are acridinium ester and acridinium acylsulfonamide groups which intercalate in a double-stranded nucleic acid. Additionally suitable is a luminol, an isoluminol or a derivative thereof, a dioxetane, a luciferin, an oxalic acid ester or an oxamide.

Luminescent compounds already find various uses. They are employed as indicators in enzyme immunoassays, luminescence immunoassays (See W. P. Collins *Alternative Immunoassays*, Publishers John Wiley & Sons Ltd., Chichester, 1985), hereby incorporated by reference, and bioassays (tests which are based not on antigen-antibody interactions, but on binding affinities between molecules which are not considered part of the immune system), but also in nucleic acid hybridization assays (See J. A. Matthews et al. *Analytical Biochemistry*, 151, 205–209, 1985), hereby incorporated by reference. Additionally, chemiluminescence compounds are used in flow injection analysis, in post-column detectors in liquid chromatography, in flow research and for the production of artificial light sources. Acridine derivatives are furthermore suitable in test methods for foodstuff and environmental analysis.

The use of acridinium labels in nucleic acid hybridization assays is mentioned in EP-A-0 273 115 and also in EP-A-0 212 951, EP-A-0 281 390, EP-A-0 310 312, EP-A-0 313 219 and WO 89/02896, all of which are hereby incorporated by reference. EP-A-0 407 816, hereby incorporated by reference, describes nucleotide derivatives with the base uracil, which for its part is labeled with a chemiluminescence compound via a spacer. EP-A 602 524, hereby incorporated by reference, describes luminescent-labeled gene probes with properties which are advantageous compared with the prior art, and, inter alia, a homogeneous gene probe assay according to the hybridization protection assay principle, which is based on the advantageous properties of the gene probes disclosed.

Anti-label Antibodies

Antibodies directed against the label can basically be prepared in a conventional manner, e.g. by immunizing an experimental animal with the label and subsequent selection of suitable signal-affecting antibodies. Both polyclonal and monoclonal antibodies are suitable, monoclonal antibodies (MAbs) being preferred. Monoclonal antibodies can be produced in various ways using techniques well-understood by those having ordinary skill in the art. Details of these techniques are described in *Antibodies: A laboratory manual*, Harlow et al., Cold Spring Harbor Publications, p. 726 (1988), hereby incorporated by reference. Some antibodies directed against luminogenic acridinium labels have the property, by binding the label, of reducing its signal strength (quench effect). Thus, for example, in a single experimental batch under 10 mouse MAbs directed against a luminogenic acridinium acylsulfonamide label were found which, with respect to possible signal-quenching properties, were not preselected and one MAb was found which had the desired signal-quenching properties.

An example of a highly suitable antibody is the monoclonal mouse antibody secreted from the cell line BW 90-614-8-04, which has been deposited in the German Collection of Microorganisms and Cell Cultures GmbH, Mascheroder Weg 13, D-38124 Brunswick under the entry number DSM ACC 2184. This MAb is directed against the acridinium acylsulfonamide shown in FIG. 2.

In accordance with the present invention, fragments of the antibody of the invention can be obtained from the antibody produced as described above, by methods which include digestion with enzymes such as pepsin or papain and/or cleavage of disulfide bonds by chemical reduction. Alternatively, antibody fragments encompassed by the present invention can be synthesized using an automated peptide synthesizer as supplied by Applied Biosystems, Multiple Peptide Systems, etc., or they may be produced manually, using techniques well known in the art. See Geysen, et al. *J. Immunol. Methods* 102: 259–274 (1978).

Antibodies can be chemically modified in accordance with the present invention by techniques well-known to the skilled artisan. See, e.g. Ritter, M. A. et al., *Monoclonal antibodies, Production, engineering and clinical application*, Chapter 8, Cambridge University Press (1995) and Birch, J. R., *Monoclonal Antibodies, Principles and Applications* pp. 137–230, Wiley-Liss, Inc. (1995), both of which are hereby incorporated by reference.

Preparation of the Gene Probes

The preparation of suitable gene probes can be performed using methods known in principle to the person skilled in the art. Gene probes are discussed in detail in a relatively large number of publications, for example in: S. L. Beaucage and R. P. Iyer: *The Functionalization of Oligonucleotides Via Phosphoramidite Derivatives*, Tetrahedron 49, 1925–1963 (1993) and J. Goodchild: *Conjugates of Oligonucleotides and Modified Oligonucleotides: A Review of Their Synthesis and Properties*, Bioconjugate Chemistry 1, 165–187 (1990), both of which are hereby incorporated by reference.

Figure 3:
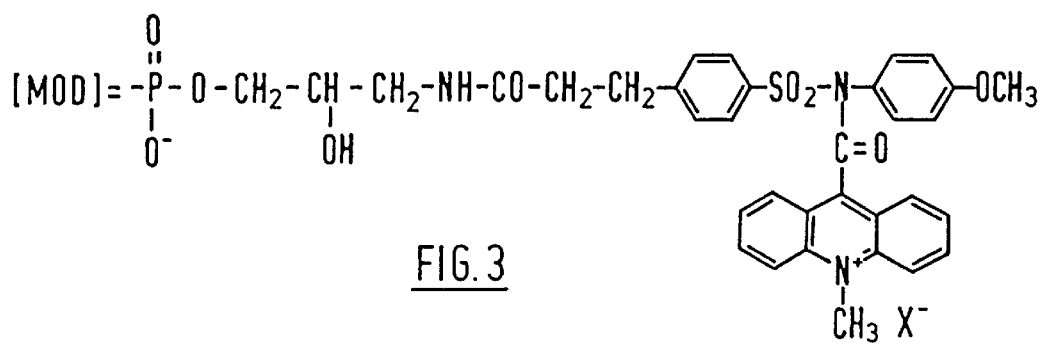
FIG. 3 shows the structure of a gene probe that is labeled, according to the invention.

The structure of a suitable gene probe is shown by way of example in FIG. 3. Of course, the nucleotide base sequence shown can be replaced by any other suitable sequence. Other labels known to any person skilled in the art can also be linked to the nucleic acid to be used as a gene probe by methods known to any person skilled in the art.

The Gene Probe Assay

Generally, the method according to the invention can be realized on the basis of all methods known in the prior art. For instance, the skilled artisan would know to adjust hybridization and stringency conditions in accordance with well-known procedures. See e.g., Ausubel et al., *Current Protocols in Molecular Biology,* Chapter 6, Wiley Interscience (1994). The gene probe technology according to the invention can advantageously be employed in homogeneous tests that do not involve a physical separation step between nucleic acid hybridization and signal detection. On account of the strong signal quench by an anti-label MAb, substantially more sensitive homogeneous gene probe tests can be developed, with comparatively good stability, than are known in the prior art. Homogeneous gene probe assays according to the invention are additionally distinguished by simple handling and easy automatability.

Figure 4A:
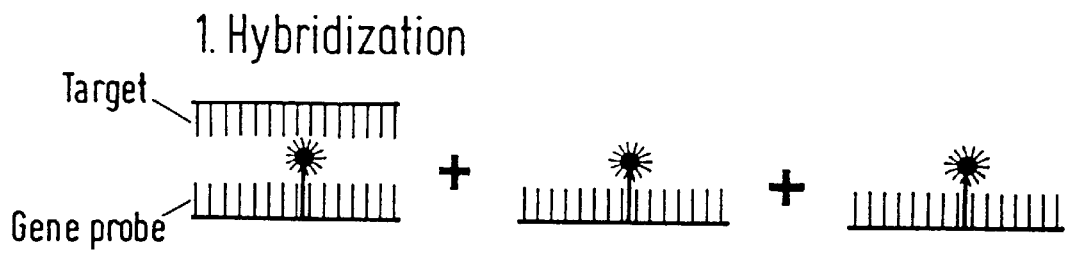
FIGS. 4(a)–4(c) schematically represent the homogenous gene probe assay of the present invention.
Figure 4B:
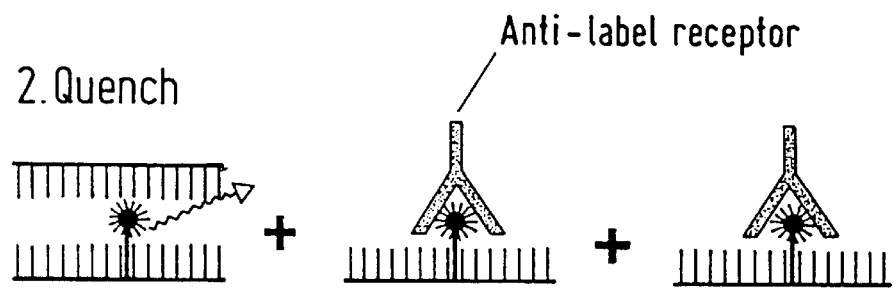
Figure 4C:
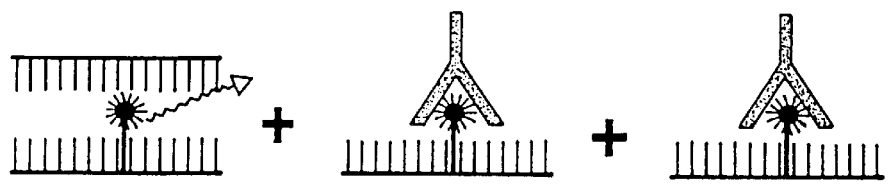
Figure 5A:
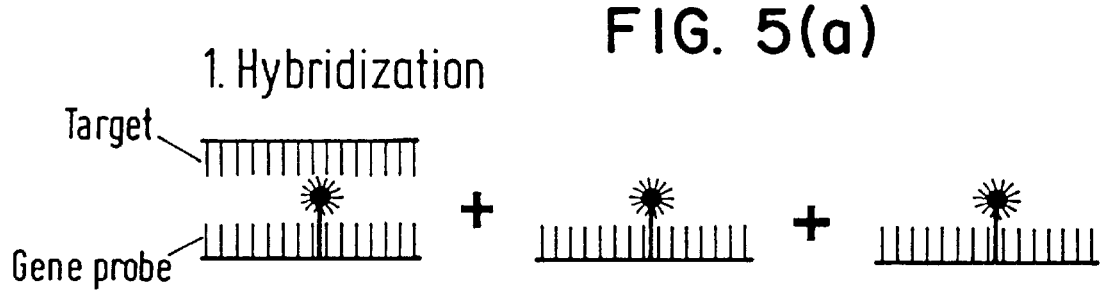
FIGS. 5(a)–5(d) schematically represent the homogenous gene probe assay of the invention, wherein after the first hybridization step, a selective hydrolysis of the single stranded gene probe is accomplished by a selection reagent and only subsequently, a receptor against the label is employed.
Figure 5B:
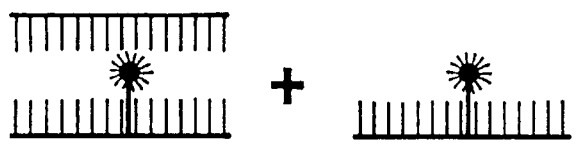
Figure 5C:
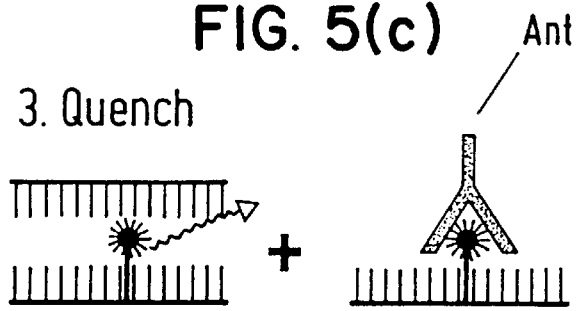
Figure 5D:
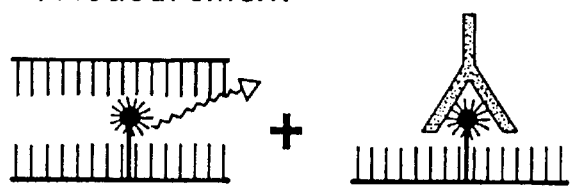

A preferred variant of the method according to the invention is shown schematically in FIGS. 4(a)–4(c): in the first step, the target sequence and labeled gene probe are hybridized with one another, wherefrom doublestranded constructs result if there is sufficient homology of the two sequences. Moreover, as a rule, nonhybridized single-stranded portions of the gene probe also remain. In the second step, a receptor, for example an antibody, is employed which can bind to the label of the single-stranded gene probe and, as a result of the binding, detectably alters, for example attenuates (quenches) the signal to be attributed to the label. In the third step, the signal produced by the label bound in the double-stranded construct is then almost exclusively measured, as the label of the hybridized gene probe cannot be bonded or can be bonded less well by the receptor than the label of the nonhybridized gene probe. Measuring methods include, but are not limited to, measuring by way of a luminometer according to procedures well-known to the skilled artisan. Compared with known methods, the assay of the present invention has the advantage that still less single-stranded gene probe produces an (undesired) contribution to the measured signal.

The above method can be further improved by performing, after the first hybridization step, a selective hydrolysis of the single-stranded gene probe by treatment with a selection reagent and only subsequently thereto employing a receptor directed against the label, as shown above. The measurement which then follows is virtually no longer distorted by unbound label due to the prior double elimination (hydrolysis and quenching of the label) of the label of the single-stranded gene probe (see FIGS. 5(a)–5(d)).

A further preferred working variant is based on the hybridization protection assay (See Clin. Chem 35/8: 1588–1594 (1989)) and comprises, according to the invention, detectably altering, e.g. quenching, the label of the nonhybridized single-stranded portions of the gene probe in a further step by addition of a receptor which can bind to the label of the single-stranded gene probe such that these unbound gene probes can cause no distortion of the measured signal.

The receptor employed in the method according to the invention is preferably a signal-quenching monoclonal or polyclonal antibody directed against the label, as already described further above.

The following examples are intended to illustrate the present invention further, but not to restrict it in any manner.

Example 1: Preparation of a Monoclonal Antibody Against a Luminogenic Acridinium Acylsulfonamide Label For the preparation of monoclonal antibodies, BALB-C mice were injected subcutaneously or intraperitoneally with 10 μg of acridinium acylsulfonamide-BSA conjugate, emulsified in complete Freund's adjuvant. The acridinium acylsulfonamide-BSA conjugate can be prepared by reaction of N-(4-methoxyphenyl)N-[4-(2-succinimidyloxycarbonylethyl) benzenesulfonyll-10-methylacridinium-9-carboximide fluorosulfonate or trifluoroacetate (FIG. 2) with BSA by methods known to the person skilled in the art. Four to five additional immunizations without adjuvant followed every four weeks. The last four days before the fusion the mice received intravenous booster injections (10 μg per day).

For the production of hybridomas, the immunized animals were killed by means of cervical dislocation. The spleen was aseptically removed and teased apart in order to obtain an individual suspension of spleen cells in serum-free Dulbeccols modified Eagle's medium (DMEM). The cells were collected by means of centrifugation (5 min.; 1800 rpm) and washed once in DMEM. The total cell count was determined by hemocytometer counting using the Trypan Blue exclusion technique. The mouse myeloma cells (SP2/0) were washed twice in serum-free DMEM, collected by means of centrifugation (10 min., 1000 rpm) and counted as described above.

Approximately $10^8$ spleen cells were mixed with $2\times10^7$ SP2/0 myeloma cells from the mouse. After centrifugation at 1000 rpm for 10 minutes, the supernatant was removed and 1 ml of polyethylene glycol (PEG 4000, Merck, 50%) was added to the vessel containing the pellet. The pellet was then resuspended with light tapping and incubated at 37° C. for 1 minute.

10 ml of serum-free DMEM were added dropwise with light tapping and the mixture was incubated for 2 to 4 minutes. The fused cells were then centrifuged at 1000 rpm for 10 minutes. The cell pellet obtained was suspended in DMEM containing 20% fetal calf serum (FCS) and HAT (hypoxanthine 0.1 μM; aminopterin 0.4 μM; thymidine 16 μM) and plated out onto culture plates (Nunc) with 24 wells using a concentration, by way of approximation, of $5\times10^4$–$10^6$ cells per well. After 2 to 3 weeks, individual cell colonies were removed from the individual wells and cultured in wells of a new culture plate.

The culture supernatants were examined for antigen-specific antibodies by means of the EIA technique. Each well of a microliter plate coated with acridinium acylsulfonamide-BSA (3 μg/ml) was filled with 100 μl of the supernatant and incubated at room temperature for 1 hour. After washing, 100 μl of a rabbit anti-mouse peroxidase (POD) conjugate were added at room temperature for a further hour. After incubation with the substrate for 30 minutes, the color development at 492 nm was read off on a Behring-ELISA processor (BEP). Hybridomas which produce antibodies having a suitable antigen specificity were selected and cloned using an individual cell manipulator. For the preparation of large amounts of monoclonal antibodies, the clones were replicated in mass culture. The subsequent purification of the individual monoclonal antibodies was carried out by means of protein A chromatography.

Example 2: Preparation of a Gene Probe (FIG. 3)

The synthesis of the oligonucleotide is described in EP-A 0 602 524, p. 49, Example 14(b), hereby incorporated by reference. Coupling with the acridinium acylsulfonamide was carried out by known methods, which are described, for example, in the above mentioned European Patent Application.

Example 3: Homogenous Gene Probe Test for Detection on E. coli without Anti-Label MAb 50 µl of standard (from Flash Track® test of Gen Probe, Lot 11276/11278 for positive/negative standard) are pipetted into polystyrene tubes. 50 µl of the gene probe according to FIG. 3 ($2.5 \times 10^6$ RLU, 1M tris buffer, pH 7) are added and hybridized at 60° C. for 15 minutes. 300 µl of a selection reagent (0.2M tetraborate, pH 8) are then added, shaken for 2×3 seconds and again incubated at 60° C. for 15 minutes. After this, the tubes are allowed to cool for 5 minutes.

Measurement is carried out by addition of 300 µl in each case of analyzer reagent 1 (0.1M $HNO_3$, 0.5% $H_2O_2$) and analyzer reagent 2 (0.25M NaOH) in a luminometer (AutoCliniLumat® from Berthold). The measurement time is 1 sec/sample.

A clear signal differentiation between positive and negative standard is determined (see Table 1).

Example 4: Homogeneous Gene Probe Test for the Detection of E. coli Using Anti-Label MAb 50 µl of standard (from Flash Track® test of Gen Probe, Lot 11276/11278 for positive/negative standard) are pipetted into polystyrene tubes. 50 µl of the gene probe according to FIG. 3 ($2.5 \times 10^6$ RLU, 1M tris buffer, pH 7) are added and hybridized at 60° C. for 15 minutes. 300 µl of a selection reagent (0.2M tetraborate, pH 8) are then added, shaken for 2×3 seconds and again incubated at 60° C. for 15 minutes. After this, the tubes are allowed to cool for 5 minutes.

50 µl of anti-label MAb solution (10 µg/ml of tris buffer pH 7.4, 1M, 0.1% Triton X-100) are then incubated at RT for 1 minute.

Measurement is carried out by addition of 300 µl in each case of analyzer reagent 1 (0.1M $HNO_3$, 0.5% $H_2O_2$) and analyzer reagent 2 (0.25M NaOH) in a luminometer (AutoCliniLumat® from Berthold). The measurement time is 1 sec/sample.

In comparison with the original hybridization protection assay (Example 3), the signal differentiation between positive and negative standard is clearly improved by addition of the anti-label MAb (see Table 1). A signal differentiation is achieved which otherwise is only possible in a heterogeneous embodiment using magnetic particles as the solid phase (see EP-A-0 602 524, pp. 50 to 51, Example 17, hereby incorporated by reference).

Example 5: Homogeneous Gene Probe Test for the Detection of E. coli Using Unspecific MAb (Control Experiment)

50 µl of standard (from Flash Track® test of Gen Probe, Lot 11276/11278 for positive/negative standard) are pipetted into polystyrene tubes. 50 µl of the gene probe according to FIG. 3 ($2.5 \times 10^6$ RLU, 1M tris buffer, pH 7) are added and hybridized at 60° C. for 15 minutes. 300 µl of a selection reagent (0.2M tetraborate, pH 8) are then added, shaken for 2×3 seconds and again incubated at 60° C. for 15 minutes. After this, the tubes are allowed to cool for 5 minutes. 50 µl of anti-TSH MAb solution (1 µg of TSH MAb from Medix, batch No.: SPHY052/ml of tris buffer pH 7.4, 1M, 0.1% Triton X-100) are then incubated at RT for 5 minutes.

Measurement is carried out by addition of 300 µl in each case of analyzer reagent 1 (0.1M $HNO_3$, 0.5% $H_2O_2$) and analyzer reagent 2 (0.25M NaOH) in a luminometer (AutoCliniLumat® from Berthold).

The measurement time is 1 sec/sample.

The signal differentiation between positive and negative standard corresponds—as expected—to Example 3 (see Table 1).

TABLE 1

|  | Example 3 | Example 4 | Example 5 |
| --- | --- | --- | --- |
| Positive Std. | 13449 | 14229 | 13872 |
| [RLU] | 14066 | 14041 | 14119 |
| Negative Std. | 416 | 53 | 408 |
| [RLU] | 404 | 47 | 419 |

(RLU = relative light units)

Priority application, German application No. 195 34 122.8, filed Sep. 14, 1995, including the specification, claims, drawing and abstract, is hereby incorporated by reference.

We claim:

1. A method of detecting a target nucleotide sequence in a sample, said method comprising:

(a) contacting a sample suspected of containing a target nucleotide sequence with a labeled gene probe capable of hybridizing with said target nucleotide sequence so that said target nucleotide sequence hybridizes with part, but not all of said labeled gene probe in said sample;

(b) adding to said sample containing said target nucleotide sequence and hybridized labeled gene probe and non-hybridized labeled gene probe, a receptor which binds said non-hybridized labeled gene probe, but wherein the label of said hybridized labeled gene probe cannot be bound by said receptor or is bound to a lesser extent than the label of said non-hybridized labeled gene probe, whereby the binding of said receptor to said non-hybridized labeled gene probe alters the signal generated by said label of said non-hybridized labeled gene probe, wherein said receptor is selected from the group consisting of a monoclonal antibody, a polyclonal antibody, an antibody fragment, a chemically modified antibody and a chemically modified antibody fragment and said label is selected from the group consisting of an acridinium ester, an acridinium acylsulfonamide, a luminol, an isoluminol, or a derivative thereof, a dioxetane, a luciferin, an oxalic acid ester and an oxamide; and (c) detecting the labeled gene probe that is hybridized to said target nucleotide sequence, thereby detecting said target nucleotide sequence.

2. The method of claim 1, further comprising, prior to the addition of said receptor in step (b), incubating said non-hybridized gene probe with a selection reagent thereby partly inactivating said label on said non-hybridized gene probe.

3. The method of claim 1, wherein said receptor is a monoclonal antibody.

4. A method of detecting a target nucleotide sequence in a sample according to claim 1, wherein said method is a homogeneous method, wherein there is an absence of a physical separation step between steps (a) and (c).

* * * * *